US00PP11724P

United States Patent [19]

Osiecki

[11] Patent Number: Plant 11,724

[45] Date of Patent: Dec. 26, 2000

[54] PHILODENDRON PLANT NAMED 'CONGO'

[75] Inventor: Marian W. Osiecki, Marianna, Fla.

[73] Assignee: Oglesby Plants International, Inc., Altha, Fla.

[21] Appl. No.: 09/250,521

[22] Filed: Feb. 16, 1999

[51] Int. Cl.[7] ..... A01H 5/00

[52] U.S. Cl. ..... Plt./381

[58] Field of Search ..... Plt./381

*Primary Examiner*—Bruce R. Campell
*Assistant Examiner*—Kent L. Bell
*Attorney, Agent, or Firm*—C. A. Whealy

[57] ABSTRACT

A new and distinct cultivar of Philodendron named 'Congo' particularly characterized by its self-heading, not vining, and self-supporting appearance; large plant size; mostly upright, somewhat outwardly spreading and open plant habit; good vigor and rapid growth rate; early and freely branching; large, thick, leathery and glossy dark green leaves; and relatively long petioles with long, slightly grayed orange-colored petiole sheaths.

2 Drawing Sheets

BACKGROUND OF THE INVENTION

The present invention relates to a new and distinct cultivar of Philodendron plant, botanically known as *Philodendron tatei* Krause spp. *melanochlorum* (Bunting) Bunting, and hereinafter referred to by the cultivar name 'Congo'.

The new Philodendron is a product of a planned breeding program conducted by the Inventor in Altha, Fla. The objective of the breeding program was to develop new Philodendrons that were self-heading, not vining, and self-supporting with distinctive plant form and growth habit, thick leaves, rapid growth rate and shorter petioles than plants of the parent selection.

The new Philodendron originated from a self-pollination made by the Inventor on Aug. 19, 1993, of an unidentified selection of the *Philodendron tatei* Krause spp. *melanochlorum* (Bunting) Bunting. The cultivar 'Congo' was discovered and selected by the Inventor on Apr. 21, 1995, as a fully grown plant in a 20-cm container within the progeny of the self-pollination in a controlled environment in Altha, Fla.

Compared to plants of the parent selection, plants of the new Philodendron are more vigorous, branch earlier, are more freely branching, and have a fuller plant habit and shorter petioles.

Asexual propagation of the new Philodendron by tissue culture at Altha, Fla. has shown that the unique features of this new Philodendron plant are stable and reproduced true to type in successive generations.

SUMMARY OF THE INVENTION

The new Philodendron has not been observed under all possible environmental conditions. The phenotype may vary somewhat with variations in environment such as temperature, light intensity, fertilizer rate, and/or irrigation amount and frequency without, however, any variance in genotype.

The following traits have been repeatedly observed and are determined to be the unique characteristics of 'Congo'. These characteristics in combination distinguish 'Congo' as a new and distinct cultivar:

1. Plants of the new Philodendron are self-heading, not vining, and are self-supporting.

2. Plants of the new Philodendron are relatively large in size with a mostly upright, somewhat outwardly spreading and open plant habit.

3. Plants of the new Philodendron are vigorous and have a rapid growth rate.

4. Plants of the new Philodendron branch early and are freely branching.

5. Plants of the new Philodendron have large, thick, leathery and glossy dark green leaves.

6. Plants of the new Philodendron have relatively long petioles and long, slightly grayed orange-colored petiole sheaths.

Plants of the new Philodendron can be compared to plants of the commercial Philodendron cultivar 'Imperial Green', disclosed in U.S. Plant Pat. No. 6,086. However, in side-by-side comparisons conducted in Altha, Fla., plants of the new Philodendron differ from plants of the cultivar 'Imperial Green' in the following characteristics:

1. Plants of the new Philodendron are larger and are more outwardly spreading and open than plants of the cultivar 'Imperial Green'.

2. Plants of the new Philodendron are more vigorous, form branches earlier and are more freely branching than plants of the cultivar 'Imperial Green'.

3. Leaves of plants of the new Philodendron are thicker, more ovate in shape with truncate bases, and have more numerous primary veins than leaves of plants of the cultivar 'Imperial Green'.

4. Leaf color of plants of the new Philodendron is darker green and there is a more striking contrast between the midrib and the surrounding leaf tissue compared to leaves of plants of the cultivar 'Imperial Green'.

5. Plants of the new Philodendron have longer and narrower petioles than plants of the cultivar 'Imperial Green'. In addition the shape of the petiole also differs.

6. Leaf petiole of sheaths of plants of the new Philodendron are greener and lighter in color than leaf petiole sheaths of plants of the cultivar 'Imperial Green'.

Plants of the new Philodendron can also be compared to plants of the commercial Philodendron cultivar 'Imperial Red', disclosed in U.S. Plant Pat. No. 6,337. However, in side-by-side comparisons conducted in Altha, Fla., plants of the new Philodendron differ from plants of the cultivar 'Imperial Red' in the following characteristics:

1. Plants of the new Philodendron are larger and are more outwardly spreading and open than plants of the cultivar 'Imperial Red'.

2. Plants of the new Philodendron are more vigorous, form branches earlier and are more freely branching than plants of the cultivar 'Imperial Red'.

3. Leaves of plants of the new Philodendron are thicker, more ovate in shape with truncate bases, and have more numerous primary veins than leaves of plants of the cultivar 'Imperial Red'.

4. Leaf color of plants of the new Philodendron is green whereas leaf color of plants of the cultivar 'Imperial Red' is maroon. Additionally, there is a more striking contrast between the midrib and the surrounding leaf tissue on plants of the new Philodendron compared to leaves of plants of the cultivar 'Imperial Red'.

5. Plants of the new Philodendron have longer and narrower petioles than plants of the cultivar 'Imperial Red'. In addition the shape of the petiole also differs.

6. Leaf petiole sheaths of plants of the new Philodendron are greener and lighter in color than leaf petiole sheaths of plants of the cultivar 'Imperial Red'.

7. Plants of the new Philodendron flower later than plants of the cultivar 'Imperial Red'.

BRIEF DESCRIPTION OF THE PHOTOGRAPHS

The accompanying colored photographs illustrate the overall appearance of the new Philodendron, showing the colors as true as it is reasonably possible to obtain in colored reproductions of this type.

The photograph on the first sheet comprises a top perspective view of a typical plant of 'Congo' in a 15-cm container.

The photograph at the top of the second sheet comprises a close-up view of the upper surface of a mature leaf.

The photograph at the bottom of the second sheet comprises a close-up view of the lower surface of a mature leaf. Leaf colors in the photographs may appear different from the actual colors due to light reflectance.

DETAILED BOTANICAL DESCRIPTION

The following observations, measurements and comparisons describe plants grown in Altha, Fla., under a polycarbonate-covered greenhouse and conditions which closely approximate those used in commercial horticultural practice. Plants were grown under day temperatures ranging from 25 to 32° C. and night temperatures ranging from 22 to 27° C. Light level ranged from 800 to 2,000 footcandles.

Plants used for this description were asexually reproduced in tissue culture, rooted and planted into 15-cm containers. Information was collected for this description and the cultivar comparisons in January, 1999, when the plants were about 15 months old from a tissue culture-produced microcutting. Numerical measurements represent averages from typical plants.

In the following description, color references are made to The Royal Horticultural Society Colour Chart except where general terms of ordinary dictionary significance are used.

Botanical classification: *Philodendron tatei* Krause spp. *melanochlorum* (Bunting) Bunting cultivar 'Congo'.

Parentage: Self-pollination of an unidentified selection of *Philodendron tatei* Krause spp. *melanochlorum* (Bunting) Bunting.

Propagation:

*Type.*—By tissue culture.

*Time to initiate roots.*—Summer: About 21 days at about 25 to 30° C. Winter: About 28 days at about 22 to 27° C.

*Time to develop* (*Time to produce a rooted liner*).—Summer: About 10 to 12 weeks at about 25 to 30° C. Winter: About 13 to 14 weeks at about 22 to 27° C.

*Rooting habit.*—Strong root system. Main roots thick and fleshy; abundant thin lateral roots. Thick short aerial roots are occasionally observed.

Plant description:

*Growth habit.*—Self-heading, not vining, and self-supporting. Mostly upright, but outwardly spreading; open; freely branching; somewhat asymmetrical; mature plants, more rounded in overall shape. Appropriate for 15 to 25-cm containers.

*Plant size.*—Height, soil surface to top of leaf canopy: About 50.7 cm. Width: About 99.2 cm.

*Plant vigor.*—Vigorous, rapid growth rate.

*Crop time.*—About 48 to 52 weeks are required to produce a 40 to 50-cm tall plant in a 15-cm container from a 1 to 2-cm tissue culture-produced microcutting.

*Foliage description.*—Shape of leaves on young plants: Between elliptic and ovate; apex, acuminate with some acute tendencies; base, obtuse; margin, entire. Shape of leaves on older plants: Ovate; apex, acuminate with some acute tendencies; base, truncate; margin, entire. Length, mature leaves: About 36.7 cm. Width, mature leaves: About 18.8 cm. Length to width ratio, mature leaves: About 1.95 to 1. Aspect: Almost flat; slightly concave at the petiole attachment. Texture: Thick, leathery, smooth. Surface: Glossy; young leaves very glossy. Color: Young, upper surface: At unrolling: Slightly darker than 144A. Once unrolled: Much darker than 144A. Young, lower surface: 144A. Mature, upper surface: Darker than 147A. About 1 mm wide band along margin, lighter green, 144A. Mature, lower surface: Darker and slightly greener than 144A; with subsequent development, leaf becomes slightly darker and greener than 147B. Venation, upper surface of mature leaves: Midrib adjacent to petiole, 144B to 146B to 146C with short darker green striae; distal, darker green, 147A. Primary veins are slightly lighter green than surrounding leaf tissue. Venation, lower surface of mature leaves: Midrib and primary veins, mostly 146C. Petiole aspect: Erect to semi-erect. Petiole shape: Rounded lower surface; upper surface slightly concave. Petiole length, primary shoot: About 43.4 cm. Petiole diameter, just below leaf blade: About 10.3 mm. Petiole sheath length: About 21.2 cm. Petiole color, young leaves: 144A to 146C with short darker green striae. Petiole color, upper surface of mature leaves: Adjacent to leaf blade, close to 146A to 146B with some 144A; proximally darker to 146A to 147B; slightly lighter near base. Short darker green striae. Petiole color, lower surface of mature leaves: Adjacent to leaf blade, close to 146B to 146D and 144A to 144B; proximally darker, close to 146A; base, close to 144A. Short darker green striae. Petiole sheath: 144B and 144D with short darker green striae; some grayed orange, close to 166C to 166D, present at proximal end near edges, more noticeable at distal end.

*Inflorescence.*—Typical of Philodendron, no commercial significance. Plants typically form inflorescences about 18 to 23 months after planting of a tissue culture-produced microcutting. Description of inflorescences taken from plants grown for about 2.5 years after planting a tissue culture-produced microcutting.

*Arrangement.*—Spathes with spadices with one to three inflorescences in each floral sympodium. Each developing inflorescense enclosed by two sheaths, which deteriorate before spathe opens. Spathes erect, situated near shoot base on short, thick, usually bent peduncles. Spathes typically tightly tolled around spadices; spathes typically open for about one day. When spathes are open, the spadix is fully exposed, leaning forward beyond spathe margins, at about 50° to penduncle axis.

*Fragrance.*—Strong, pleasant; similar to Hyacinth, but weaker.

*Peduncle.*—Length: About 7.3 cm. Diameter: About 1.5 cm. Color: 144B or between 144B and 144C.

*Spathe.*—Shape: Boat-shaped; longitudinal section elliptic; apex between acuminate and cuspidate; base, obtuse; margin, entire and usually rolled back especially distally. Length: About 18.3 cm. Width: About 7.6 cm. Length to width ratio: About 2.4 to 1. Depth: About 4.8 cm. Texture: Very thick, fleshy, not glossy. Color: Open, front surface: Between 47A and 47B around spadix base; distally and toward margin, much lighter, 48D to 49D to close to 159C near apex with some scattered light pink. Some yellow green, 144B, on midrib and along margins near apex. Open, rear surface: Most of the central zone of proximal half is an uneven color, varying between different combinations of 146C, 146D, 144A, 144B and 144C. Color becomes lighter and more yellow towards margins; near margins, between 145C and 145D and translucent. In the distal half, there is a band along midrib between 144B, and 146C and 146D. Spathe color on either side of this band is variable, but much lighter and more yellow, most areas more yellow than 145C and more green than 150C. Often there is a wide, almost whitish, translucent band on one side near the margin.

*Spadix.*—Shape: Cylindrical, strongly tapering towards acute apex. Female zone, situated at the base, shorter than the male zone and separated by an intermediate sterile zone. Sterile and male zones not clearly distinguished when spathe is open. Spadices typically sessile. Length: About 17.1 cm; female zone, about 4.8 cm; sterile and male zones combined, about 12.6 cm. Diameter: Female zone, about 1.9 cm; sterile and male zones, about 1.8 cm proximally. Color: Female zone, between 145C and 145D; sterile and male zones, slightly darker than 159C. Pollen: Cream in color. Dehiscence about one to three days after spathe closes.

*Seed production.*—Seed production has not been observed. Typically spathes and spadices gradually deteriorate after spathe closure.

Disease tolerance: Resistance to pathogens common to Philodendron has not been observed.

It is claimed:

1. A new and distinct cultivar of Philodendron plant named 'Congo', as illustrated and described.

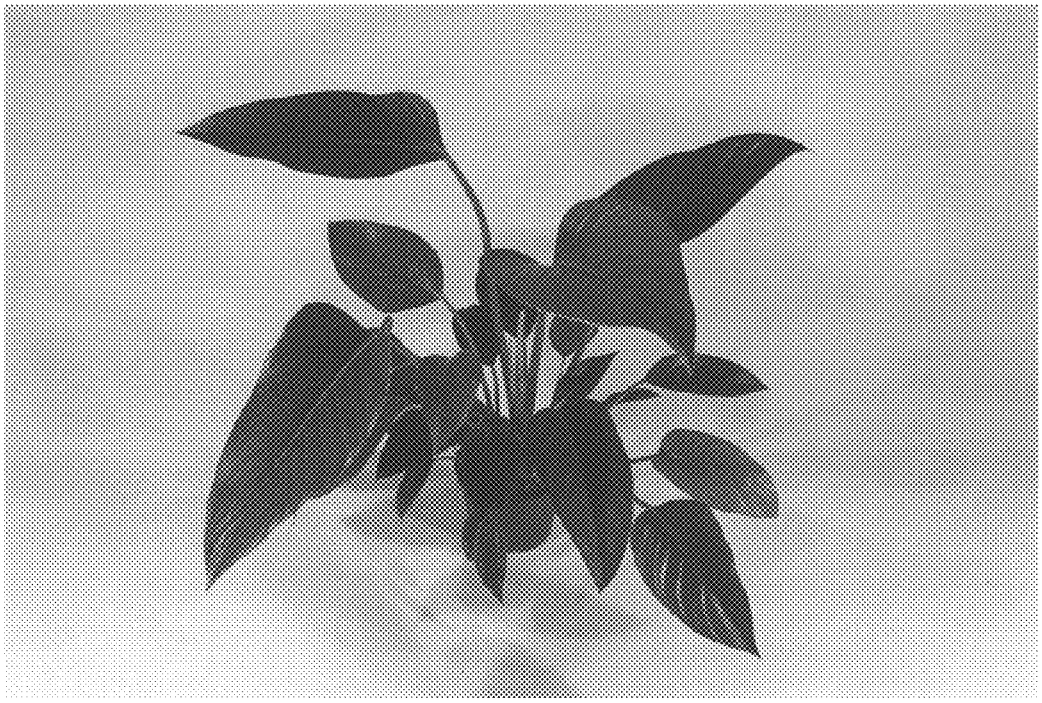

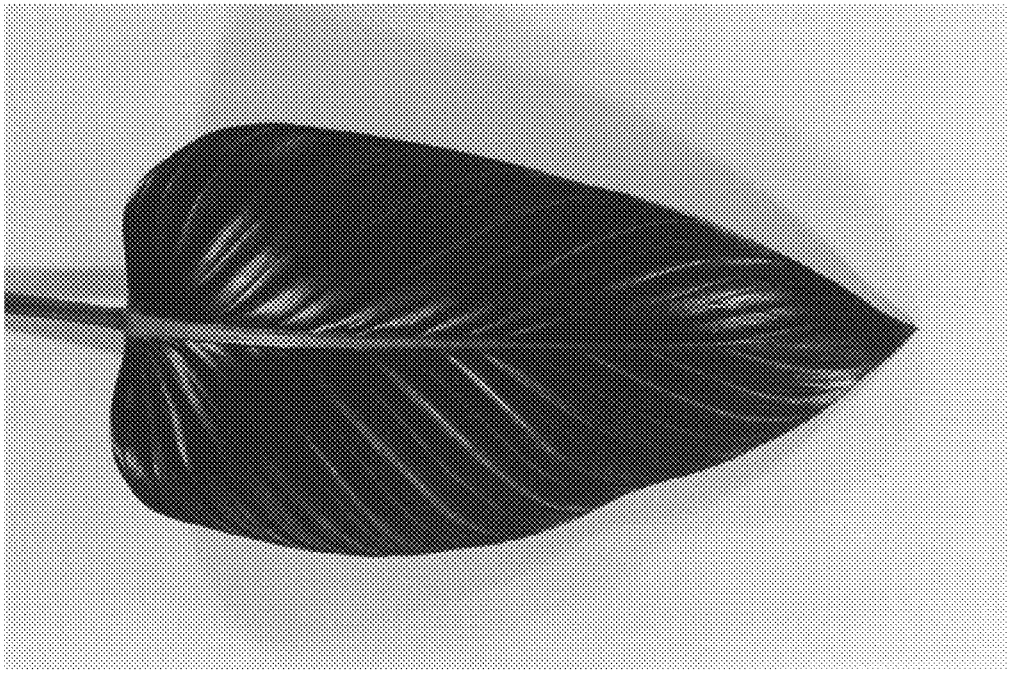
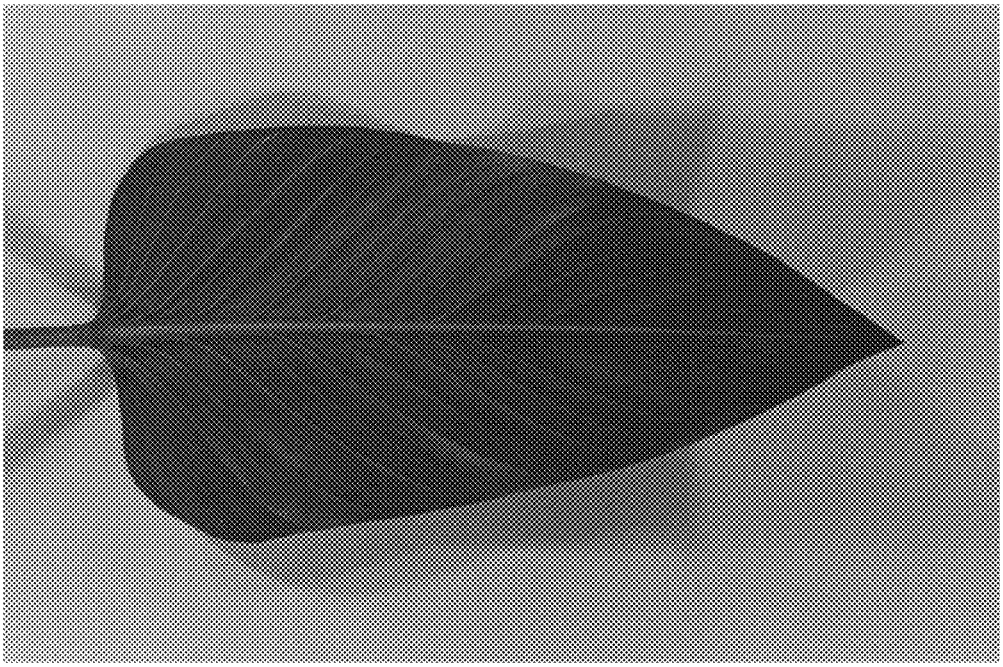

* * * * *